United States Patent [19]
Florio et al.

[11] Patent Number: 6,128,533
[45] Date of Patent: Oct. 3, 2000

[54] PACEMAKER WITH AUTOMATIC PVARP ADJUSTMENT DURING AUTOMATIC MODE SWITCHING

[75] Inventors: Joseph J. Florio, La Canada; Gregory Hauck, Valencia, both of Calif.

[73] Assignee: Pacesetter, Inc., Sylmar, Calif.

[21] Appl. No.: 09/273,403

[22] Filed: Mar. 22, 1999

[51] Int. Cl.$^7$ ................................................. A61N 1/362
[52] U.S. Cl. ................................................................ 607/9
[58] Field of Search ........................................... 607/9, 14

[56] References Cited

U.S. PATENT DOCUMENTS

| | | | |
|---|---|---|---|
| 4,485,818 | 12/1984 | Leckrone et al. | 128/419 PG |
| 4,624,260 | 11/1986 | Baker et al. | 128/419 PG |
| 4,712,555 | 12/1987 | Thornander et al. | 128/419 PG |
| 4,722,341 | 2/1988 | Hedberg et al. | 128/419 PG |
| 4,940,052 | 7/1990 | Mann et al. | 128/419 PG |
| 4,944,298 | 7/1990 | Sholder | 128/419 PG |
| 5,134,997 | 8/1992 | Bennett et al. | 128/419 PG |
| 5,231,985 | 8/1993 | Sutton et al. | 607/18 |
| 5,247,929 | 9/1993 | Stoop et al. | 128/419 PG |
| 5,282,465 | 2/1994 | Van der Veen et al. | 128/419 PG |
| 5,549,649 | 8/1996 | Florio et al. | 607/15 |
| 5,591,214 | 1/1997 | Lu | 607/9 |
| 5,609,610 | 3/1997 | Nappholz | 607/9 |
| 5,788,717 | 6/1998 | Mann et al. | 607/14 |

*Primary Examiner*—William E. Kamm

[57] ABSTRACT

An implantable dual-chamber pacemaker programmed to operate primarily in an atrial tracking mode includes an atrial rate smoothing filter for producing a filtered atrial rate (FAR) from an intrinsic atrial rate. The pacemaker automatically switches its mode of operation from an atrial tracking mode (i.e., DDD, DDDR, VDD, VDDR, DDT or DDTR) to a non-atrial tracking mode (i.e., DDI, DDIR, VDI, VDIR, DDT or DDTR), in the event the filtered atrial rate exceeds a prescribed upper rate limit. Synchronously with this mode switch, the pacemaker automatically shortens a post ventricular atrial refractory period (PVARP) to a minimum, predefined or programmable value. In one embodiment, the shortened PVARP is set equal to a post ventricular atrial blanking period (PVAB) that ranges between approximately 50 msec and 200 msec. While in the alternate mode of operation, the pacemaker maintains the shortened PVARB refractory period, and continues to monitor the FAR. As soon as FAR drops to a preset value or below, the pacemaker automatically switches back to its primary atrial tracking mode.

49 Claims, 6 Drawing Sheets

PRIMARY ATRIAL TRACKING DDD/R MODE

SWITCHING TO ALTERNATE NON-ATRIAL TRACKING DDI/R MODE

SWITCHING TO ALTERNATE NON-ATRIAL TRACKING DDI/R MODE AND ALTERNATE PACING RATE

SWITCHING TO PRIMARY ATRIAL TRACKING DDD/R MODE

PACEMAKER WITH AUTOMATIC PVARP ADJUSTMENT DURING AUTOMATIC MODE SWITCHING

FIELD OF THE INVENTION

The present invention relates generally to programmable cardiac pacing devices, and particularly to implantable dual-chamber pacemakers capable of switching from an atrial tracking mode of operation to a non-atrial tracking mode in response to the occurrence of an atrial arrhythmia. More particularly, the present invention relates to a pacemaker that automatically shortens a post ventricular atrial refractory period (PVARP) to a minimum, predefined or programmable value, in the event the pacemaker switches its mode of operation from an atrial tracking mode (i.e., DDD, DDDR, VDD, VDDR, DDT or DDTR) to a non-atrial tracking mode (i.e., DDI, DDIR, VDI, VDIR, DDT or DDTR). The pacemaker maintains this shortened PVARP until it switches back to the atrial tracking mode. Preferably, the shortened refractory period is set equal to a post ventricular atrial blanking period (PVAB).

BACKGROUND OF THE INVENTION

Much has been described in the art about the various types of pacemakers. For example, reference is made to commonly assigned U.S. Pat. No. 4,712,555, to Thornander et al., where some helpful background information about pacemakers and the manner in which they interface with a patient's heart is presented. This patent is hereby incorporated by reference in its entirety.

In general, both single and dual-chamber pacemakers are classified by type according to a three letter code. In this code, the first letter identifies the chamber of the heart that is paced (i.e., the chamber where a stimulation pulse is delivered) with a "V" indicating the ventricle, an "A" indicating the atrium, and a "D" indicating both the atrium and ventricle. The second letter of the code identifies the chamber where cardiac activity is sensed, using the same letters to identify the atrium, ventricle, or both, and where an "0" indicates that no sensing takes place.

The third letter of the code identifies the action or response taken by the pacemaker. In general, three types of actions or responses are recognized: (1) an Inhibiting ("I") response, where a stimulation pulse is delivered to the designated chamber after a set period of time unless cardiac activity is sensed during that time, in which case the stimulation pulse is inhibited; (2) a Trigger ("T") response, where a stimulation pulse is delivered to the designated chamber of the heart a prescribed period after a sensed event; or (3) a Dual ("D") response, where both the Inhibiting mode and Trigger mode are evoked, inhibiting in one chamber of the heart and triggering in the other.

A fourth letter, "R" is sometimes added to the code to signify that the particular mode identified by the three letter code is rate-responsive, where the pacing rate can be adjusted automatically by the pacemaker, based on one or more physiological factors, such as blood oxygen level or the patient+s activity level. As used herein, "(R)", for example DDD(R), refers to the occurrence of two modes, such as DDD and/or DDDR.

Thus, for example, a DDI pacemaker is capable of sensing and pacing in both chambers, and operates in a non-atrial tracking mode. It inhibits ventricular stimulation pulses when a prior ventricular activity is sensed.

A DDDR pacemaker represents a fully automatic pacemaker which is capable of sensing and pacing in both the atrium and ventricle, and which is also capable of adjusting the pacing rate based on one or more physiological factors, such as the patient's activity level. In general, DDD(R) pacing has four functional states: (1) P-wave sensing, ventricular pacing; (2) atrial pacing, ventricular pacing; (3) P-wave sensing, R-wave sensing; and (4) atrial pacing, R-wave sensing. Advantageously, for the patient with complete or partial heart block, the P state of the DDD(R) pacemaker tracks the atrial rate which is set by the heart's SA node, and then paces in the ventricle at a rate that follows this atrial rate. Because the rate set by the SA node represents the rate at which the heart should beat in order to meet the physiologic demands of the body (at least for a heart having a properly functioning SA node) the rate maintained in the ventricle by such a pacemaker is truly physiologic.

Those skilled in the art have long recognized the advantages of using an atrial tracking pacemaker. For example, U.S. Pat. No. 4,624,260, to Baker, Jr. et al., discloses a microprocessor controlled dual-chamber pacemaker having conditional atrial tracking capability. Similarly, U.S. Pat. No. 4,485,818, to Leckrone et al., discloses a microprocessor-based pacemaker which may be programmed to operate in one of a plurality of possible operating modes, including an atrial rate tracking mode.

However, in some instances, a given patient can develop fast atrial rhythms which result from a pathologic arrhythmia such as a pathological tachycardia, fibrillation or flutter. In these cases, a DDD(R) pacemaker can pace the ventricle in response to the sensed atrial arrhythmia up to the programmed maximum tracking rate (MTR).

Sometimes it is possible at the time of implantation of a pacemaker to determine whether an atrial fibrillation, atrial flutter, or atrial tachycardia condition is going to develop. In such instances, the pacemaker can be programmed to operate in a different mode of operation, the leads can be repositioned within the heart, or other actions may be taken to minimize the likelihood of such pathologic arrhythmias occurring. However, it is not always possible at the time of implantation to determine whether a patient will develop an atrial arrhythmia after the pacemaker is implanted.

Therefore, if such pathologic arrhythmias subsequently occur, they must be treated using other techniques, such as through the administration of drugs. Needless to say, the administration of drugs normally requires the attendance of a physician. However, a physician is not always present when such pathologic arrhythmias develop, and even when a physician is available, such drugs also can undesirably suppress the ability of the SA node to increase the sinus rate during periods of exercise, emotional stress, or other physiologic stress. Thus, the use of such drugs can prevent the pacemaker from functioning as a intrinsic physiologic rate-responsive pacemaker.

As a result, attempts have been made in the art to prevent undesirable tracking of pathologic atrial arrhythmias by automatically switching the pacemaker's mode of operation from an atrial tracking pacing mode to a non-atrial tracking pacing mode. For example, U.S. Pat. No. 4,722,341, to Hedberg et al., describes an atrium-controlled pacemaker, where the pacemaker temporarily switches from an atrial tracking mode to a non-atrial tracking mode for a fixed number of stimulation pulses if the sensed atrial activity indicates an atrial arrhythmia may be developing.

U.S. Pat. No. 4,944,298, to Sholder, which is hereby incorporated by reference in its entirety, discloses an atrial tracking pacemaker with automatic mode switching capability. The pacemaker has the capability of setting a tachycardia rate limit (TRL) slightly above a maximum tracking rate (MTR), so that mode switching to a non-atrial tracking mode occurs when the TRL is exceeded. A third threshold rate is also set at a value below the MTR. The pacemaker switches back to an atrial tracking mode when the patient's atrial rate drops below this third threshold. To avoid mode switching based on a single short atrial interval between atrial events, the atrial rate is continuously averaged over several cycles. This technique effectively prevents frequent mode switches in patients whose atrial rates "hover" around the MTR.

U.S. Pat. No. 5,549,649, to Florio et al., which is hereby incorporated by reference in its entirety, describes an implantable dual-chamber pacemaker programmed to operate primarily in an atrial tracking mode. The pacemaker automatically switches its mode of operation from the atrial tracking mode to a non-atrial tracking mode in the event a filtered atrial rate exceeds a prescribed upper rate limit. This mode switching is accompanied by a corresponding switching from a primary set of operational parameter settings for the primary mode, to an alternate set of operational parameters for the alternate mode.

In general, however, atrial pacing competition could result during mode switching if the mode being switched to is a dual-chamber, non-atrial tracking mode (i.e., DDD, DDDR, VDD or VDDR), leading to atrial arrhythmia. Yet another concern associated with such mode switching is the occurrence of functional atrial undersensing that can lead to inappropriate atrial pacing. This undersensing is due to the long refractory periods in the DDI and DDIR modes, where pacing and sensing events are counted by the filter, leading to a measured filtered atrial rate that is higher than the actual atrial rate. In this condition, it is possible to delay or prevent the pacemaker from switching back to the atrial tracking mode.

Therefore, it would be desirable if the pacemaker could substantially reduce atrial pacing competition and atrial undersensing when switching from an atrial tracking mode to a non-atrial tracking mode, and to prevent mode switch lockup.

SUMMARY OF THE INVENTION

According to the present invention, atrial competition and atrial undersensing are substantially reduced by an implantable dual-chamber pacemaker programmed to operate primarily in an atrial tracking mode (i.e., DDD, DDDR, VDD, VDDR, DDT or DDTR). The pacemaker automatically switches its mode of operation from the atrial tracking mode to a non-atrial tracking mode (i.e., DDI, DDIR, VDI or VDIR) in the event of an atrial arrhythmia, such as when the filtered atrial rate exceeds a prescribed upper rate limit.

During such mode switch, the pacemaker automatically sets its post ventricular atrial refractory period (PVARP) to a minimum value, and maintains this shortened refractory period until it switches back to the atrial tracking mode. Preferably, the shortened refractory period is set equal to the post ventricular atrial blanking period (PVAB) or to a predetermined value, such as 70 msec.

The foregoing and other features of the present invention are realized by a new pacemaker that includes an operation control system, a set of leads for receiving atrial and ventricular signals and for delivering atrial and ventricular stimulation pulses, a set of amplifiers for amplifying the atrial and ventricular signals, and pulse generators for generating atrial and ventricular stimulation pulses. In addition, the pacemaker can include memory for storing operational parameters for the control system and for storing data acquired by the control system for later retrieval by the medical practitioner using an external programmer. The pacemaker also includes a telemetry circuit for communicating with the external programmer.

The pacemaker uses a filtered atrial rate (FAR) as a basis for mode switching, in order to reduce mode switching responses due to, for example, electrical noise or one-of-a-kind fast P-waves. It obtains the FAR by filtering the intrinsic atrial rate using a rate smoothing filter. The rate smoothing filter produces the FAR during each cycle by limiting the amount by which the FAR may change from cycle to cycle.

The pacemaker is programmed to operate primarily in a dual-chamber mode of operation, such as DDD(R), where the heart is paced at a rate that follows or tracks the intrinsic atrial rate up to the MTR. When the intrinsic atrial rate exceeds the MTR, the pacemaker stimulates the heart at, or near the MTR, and continues to monitor the FAR.

If the FAR exceeds a predetermined upper rate limit referred to as an atrial tachycardia detection rate (ATDR), a pathological atrial arrhythmia is deemed to exist, and the pacemaker automatically switches from its primary mode of operation to an alternate mode of operation, such as a non-atrial racking mode. Mode switching is performed to avoid acing the ventricles at an undesirably high rate during periods of non-physiologic high atrial rates.

Mode switching from the primary mode to the alternate mode is accompanied by an automatic setting of the PVARP from a primary mode operational value to an alternate mode value, wherein the PVARP is automatically shortened to a predetermined minimum value. In one embodiment, the shortened PVARP is set equal to PVAB. In another embodiment, the shortened PVARP is selectively set equal to either PVAB or to a preset value such as approximately 70 msec. The refractory periods, PVARP and PVAB are initially set by the pacemaker manufacturer, but may be programmed by a medical practitioner at the time of implantation or during the patient's follow-up visits.

Preferably, while in the alternate mode of operation, the pacemaker continues to monitor the FAR, and as soon as the FAR drops to the level of the MTR or below, the pacemaker automatically switches back to its primary atrial tracking mode or to another predetermined mode of operation. The pacemaker maintains this shortened refractory period until it switches back from the alternate mode to the primary atrial tracking mode or to such other predetermined mode of operation.

The present invention improves the performance of an automatic mode switching pacemaker and also improves the comfort of a patient by significantly reducing atrial competition and atrial undersensing, when the pacemaker switches to a particular pacing mode. The automatic setting of PVARP during mode switching alleviates the medical practitioner's burden of accounting for, and programming the operational parameters for the primary and alternate modes.

BRIEF DESCRIPTION OF THE DRAWINGS

The features of the present invention and the manner of attaining them, will become apparent, and the invention will be understood by reference to the following description and the accompanying drawings, in which like reference numerals refer to like parts, and in which.

DETAILED DESCRIPTION OF THE PREFERRED EMBODIMENTS

Figure 1:
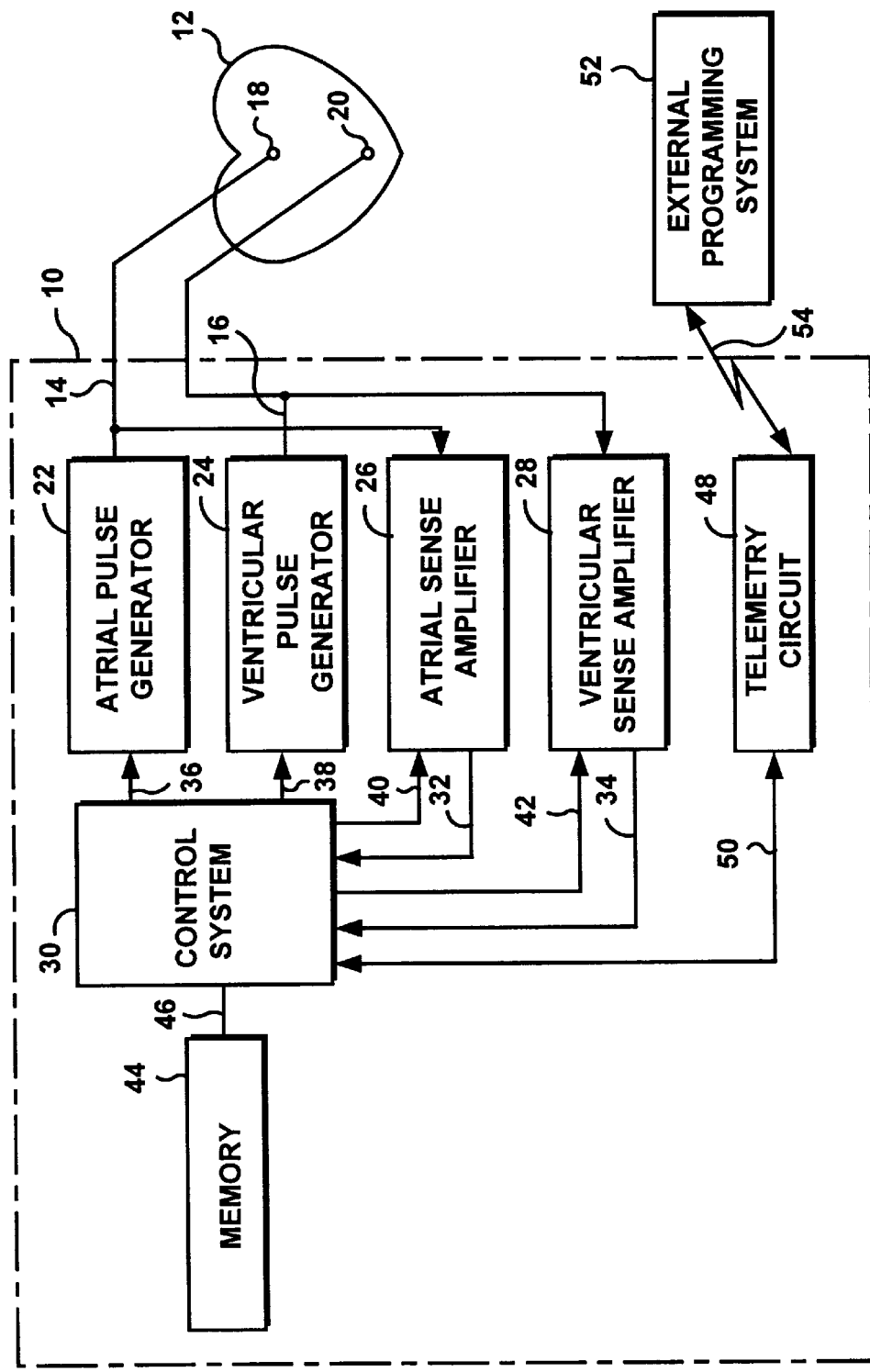
FIG. 1 is a block diagram of a mode switching pacemaker in accordance with the principles of the present invention.

A pacemaker 10 in accordance with this invention is shown in FIG. 1. The pacemaker 10 is connected to a heart 12 by way of leads 14 and 16. The lead 14 has an electrode 18 which is implanted within one of the atria of the heart 12. The lead 16 has an electrode 20 which is implanted within one of the ventricles of the heart 12. The lead 14 carries stimulating pulses to the electrode 18 from an atrial pulse generator 22, and the lead 16 carries stimulating pulses to the electrode 20 from a ventricular pulse generator 24. In addition, electrical signals from the atria are carried from the electrode 18, through the lead 14, to an input terminal of an atrial sense amplifier 26. Electrical signals from the ventricles are carried from the electrode 20, through the lead 16, to an input terminal of a ventricular sense amplifier 28.

Controlling the dual-chamber pacemaker 10 is a control system 30. The control system 30 is preferably a microprocessor-based system such as the one disclosed in U.S. Pat. No. 4,940,052, to Mann et al., which is hereby incorporated by reference in its entirety. The control system 30 may also be a state logic-based system such as the one disclosed in the U.S. Pat. No. 4,944,298, which is hereby incorporated by reference in its entirety. The control system 30 also includes a real-time clock (not shown) for providing timing to monitor cardiac events and for timing the application of therapeutic pulses by the atrial and ventricular pulse generators 22 and 24, respectively.

The control system 30 receives output signals from the atrial sense amplifier 26 over a signal line 32. Similarly, the control system 30 receives output signals from the ventricular sense amplifier 28 over a signal line 34. These output signals are generated each time that an atrial event (e.g., a P-wave or Ps) or a ventricular event (e.g., an R-wave) is sensed within the heart 12.

The control system 30 also generates an atrial trigger signal which is sent to the atrial pulse generator 22 over a signal line 36, and a ventricular trigger signal which is sent to the ventricular pulse generator 24 over a signal line 38. These trigger signals cause stimulation pulses to be generated by the pulse generators 22, 24. The atrial stimulation pulse is referred to herein as "A-pulse," and the ventricular stimulation pulse is referred to herein as "V-pulse" or Vp.

During the time that either an A-pulse or a V-pulse is being delivered to the heart 12, the corresponding atrial sense amplifier 26 or the ventricular sense amplifier 28 is typically disabled by way of a blanking signal presented to the appropriate amplifier from the control system 30 over a signal line 40 for the atrial sense amplifier 26 or a signal line 42 for the ventricular sense amplifier 28. This blanking action prevents the amplifiers 26 and 28 from becoming saturated with the relatively large stimulation pulses present at their input terminals during pacing pulse delivery. This blanking action also prevents residual electrical signals (known as "afterpotentials") present in the muscle tissue as a result of the pacemaker stimulation from being interpreted as atrial or ventricular events.

Still referring to FIG. 1, the pacemaker 10 also includes a memory 44 which is connected to the control system 30 through a suitable data bus 46. The memory 44 allows certain control parameters used by the control system 30 in controlling the operation of the pacemaker 10 to be stored and modified or programmed, as required, in order to customize the operation of the pacemaker 10 to suit the needs of a particular patient. In addition, data sensed during the operation of the pacemaker 10 (e.g., mode switching event data, as described herein) may be stored in the memory 44 for later retrieval and analysis.

The pacemaker 10 further comprises a telemetry circuit 48 which is connected to the control system 30 by way of a command/data bus 50. In turn, the telemetry circuit 48 may be selectively coupled to an external programming device 52 by means of an appropriate communication link 54. The communication link 54 may be any suitable electromagnetic link such as a radio frequency (RF) channel.

Commands can be sent by the medical practitioner to the control system 30 from the external programmer 52 through the communication link 54. Similarly, through this communication link 54 and the external programmer 52, data (either held within the control system 30, as in a data latch, or stored within the memory 44), can be transmitted remotely by the pacemaker 10 to the external programmer 52. In this manner, noninvasive communication can be established with the implanted pacemaker 10 from a remote location.

The operation of the pacemaker 10 is generally controlled by a control program stored in the memory 44 and executed by the control system 30. This control program usually includes multiple integrated program modules, with each module bearing responsibility for controlling one or more functions of the pacemaker 10. For example, one program module controls the delivery of stimulating pulses to the heart 12, while another module controls the acquisition of atrial and ventricular electrical signals. In effect, each program module is a control program dedicated to a specific function or a set of functions of the pacemaker 10.

Figure 2:
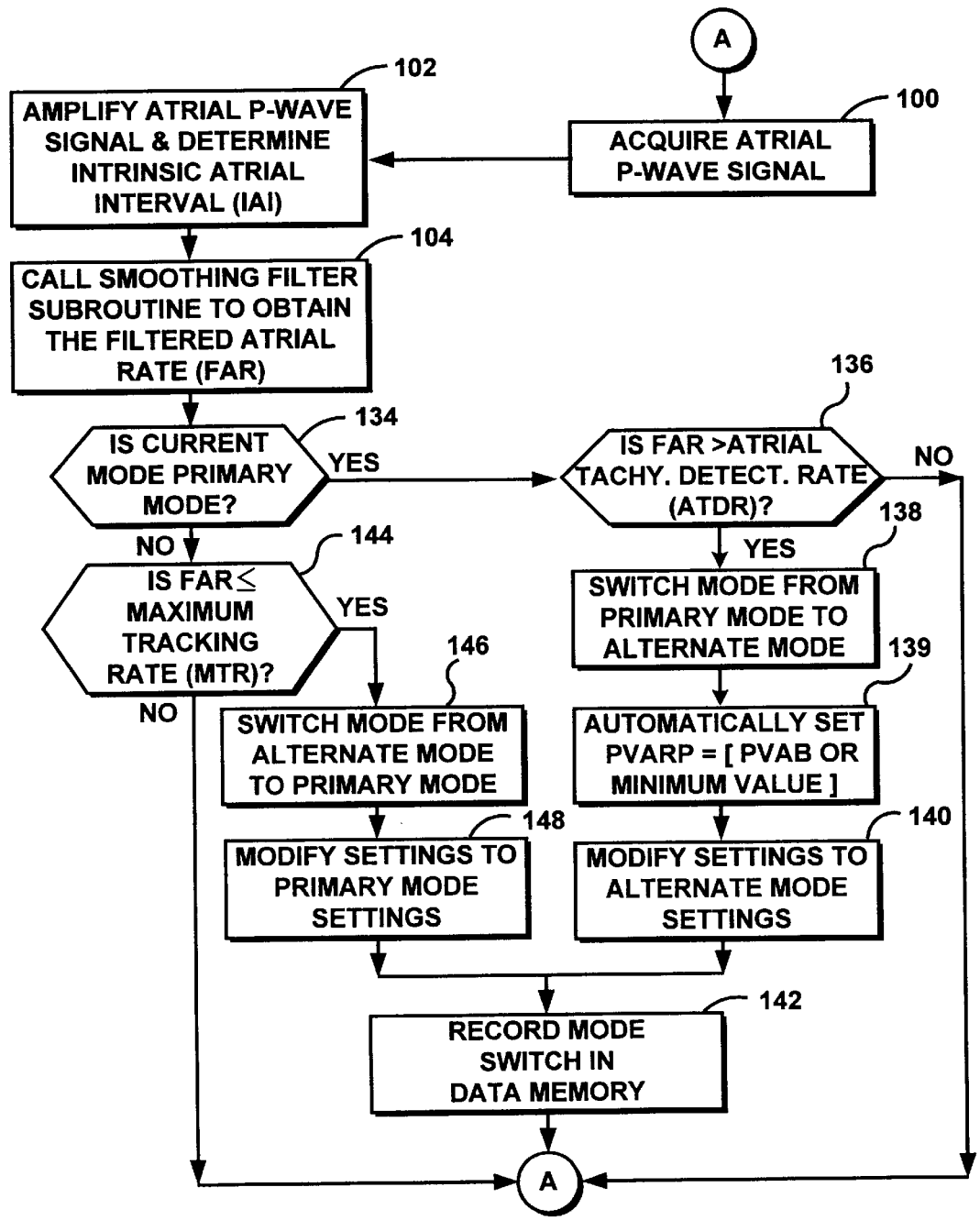
FIG. 2 depicts a logic flow diagram representing a control program executed by a microprocessor of the mode switching pacemaker shown in FIG. 1 in accordance with the principles of the present invention.

With further reference to FIG. 2, an exemplary logic flow diagram that represents an automatic mode switching control program ("control program") for the control system 30 in accordance with the present invention is depicted. This control program is executed in a loop, continuously providing the pacemaker 10 with the capability of distinguishing between a pathological arrhythmia and other conditions such as a normal sinus tachycardia or electrical noise. Preferably, one complete loop of the control program follows a single cardiac cycle. The control program also provides the pacemaker 10 with the capability of switching its mode from a primary atrial tracking mode to an alternate non-atrial tracking mode if a pathologic arrhythmia is detected, as well as the capability of switching back to the primary mode once the pathological arrhythmia subsides. Preferably, the mode switch may occur only once during a particular program cycle.

After the control program begins at step 100, the control system 30 allows the pacemaker 10 to acquire a P-wave signal from the atria of the heart 12 through the electrode 18. At step 102, the control system 30 causes the atrial sense amplifier 26 to amplify the P-wave signal, and then receives the amplified P-wave signal through the signal line 32. At step 102, the control system 30 also determines an intrinsic atrial interval (IAI) in milliseconds, by measuring the interval between the P-wave sensed during the current cardiac cycle and the P-wave sensed during the previous cardiac cycle.

When the intrinsic atrial rate exceeds the MTR, he control system 30 begins ignoring certain P-waves occurring during pacemaker refractory periods for the purpose of maintaining AV synchrony. AV synchrony is maintained under these conditions by maintaining a relatively constant AV interval with respect to those P-waves that fall outside the refractory periods. Since the P-waves occurring during the refractory periods are ignored for the purpose of maintaining AV synchrony, the control system 30 perceives an atrial rate that is lower than the intrinsic atrial rate. This lower atrial rate is referred to as the sensed functional atrial rate (SFAR). Thus, the control system 30 paces the ventricles at the SFAR, because pacing the ventricles at the intrinsic atrial rate exceeding a maximum tracking rate (MTR) set by the medical practitioner may be uncomfortable or dangerous to the patient. The MTR is typically the maximum rate at which the pacemaker 10 tracks the atrial rate when pacing the heart 12.

It is not desirable to base mode switching on the SFAR, because under certain conditions, such as 2:1 block where every other P-wave falls inside the refractory period, the SFAR may be as low as one half of the intrinsic atrial rate, and thus an inaccurate indicator of actual atrial activity. For example, in a 2:1 block condition, the patient may be experiencing a tachycardia with the intrinsic atrial rate exceeding 200 bpm, while the SFAR would indicate 100 bpm since every other atrial beat is ignored. It is therefore preferable to base mode switching on an atrial rate representative of actual atrial activity. The intrinsic atrial rate, which is indicative of actual atrial activity, is derived when all the P-waves, even the P-waves occurring during the refractory periods, are sensed by the control system 30.

Thus, to meet both objectives, the control system 30 determines the intrinsic atrial rate for the purpose of mode switching, and determines SFAR for the purpose of pacing by ignoring the P-waves occurring during the refractory periods. However, since the control system 30 is continuously sensing, its power requirements are increased.

Optionally, in pacemakers where power is limited, continuous atrial sensing may be initiated by a trigger. For example, continuous atrial sensing of the intrinsic atrial rate may be initiated if the intrinsic atrial rate exceeds a certain programmable trigger rate (PTR), the PTR preferably being less than the rate at which certain P-waves begin to be ignored by the control system 30. When the intrinsic atrial rate drops below the PTR, the continuous sensing of the intrinsic atrial rate would be disabled to conserve power.

The pacemaker 10 has the capability of tracking the intrinsic atrial rate at a rate exceeding the set MTR. Thus, an atrial tachycardia detection rate (ATDR), which is higher than the MTR, may be programmed by the medical practitioner so that the heart 12 may be paced at rates exceeding the MTR. The MTR is typically set at 80 to 180 beats per minute (bpm). The ATDR is programmable starting at 20 bpm above the MTR. This minimum 20 bpm gap allows the control system 30 to respond to pathologic arrhythmias when the intrinsic atrial rate reaches the ATDR, while avoiding responses based on slight atrial rate fluctuations above the MTR, but within the gap.

To avoid a response based on electrical noise or based on the atrial rate fluctuating above the ATDR and then below the MTR, the intrinsic atrial rate is preferably filtered. At step 104, the control system 30 calls a rate smoothing filter subroutine. Subroutines are known in the computer programming art as functions designed to perform specific tasks requested by a main program. One of the advantages of using subroutines is that two or more programs can use the same subroutine to perform a particular function. Modern programming techniques also encompass programmable "objects" which function similarly to subroutines. The main advantage of programmable "objects" is that once an "object" is developed to perform a particular function, it may be used in any program having a need to use that function. Thus, the rate smoothing filter subroutine may be used by the control system 30 for functions other than mode switching.

The rate smoothing filter subroutine ("subroutine") filters the IAI determined at the step 102 to limit atrial rate fluctuations occurring from one cardiac cycle to the next, and to minimize the effect of electrical noise. The control system 30 passes the IAI to the subroutine, and after executing the subroutine, derives a filtered atrial rate (FAR). The subroutine operates on several intervals and factors that are measured in milliseconds. An interval in milliseconds is inversely proportional to the rate in beats per minute. The operation of the subroutine is described in detail in U.S. Pat. No. 5,549,649, supra.

The control system 30 determines at decision step 134 if the pacemaker 10 is currently in a primary mode of operation by checking if a primary mode program "flag" is active. The program "flag" may be a value in one of the program memory areas of the memory 44. In this embodiment, the primary mode of operation is preferably an atrial tracking mode.

Figure 3:
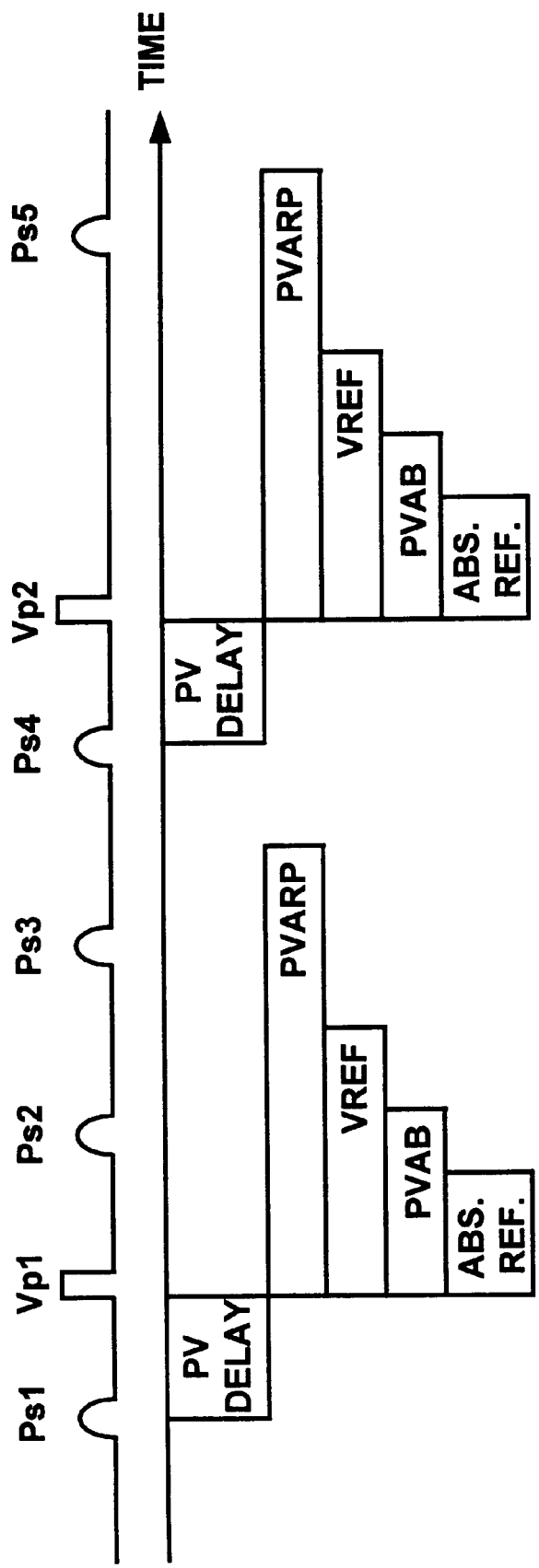
FIG. 3 is a timing diagram that illustrates the operation of the pacemaker of FIG. 1 in a primary atrial tracking DDD(R) mode.

A DDD(R) primary mode of operation is illustrated in FIG. 3. A sensed P-wave Ps1 triggers a PV delay at the end of which a ventricular stimulation pulse Vp1 is delivered. The PV delay is programmable and may range between approximately 25 msec and 350 msec. The onset of the ventricular stimulation pulse Vp1 (or the sensing of an R-wave) initiates the PVARP. In this example, the PVARP is programmable and may range between approximately 150 msec and 400 msec. All atrial events (e.g. Ps3) occurring during the PVARP but outside the PVAB are not tracked and the control system 30 issues a noise response. Atrial events (e.g. Ps3) occurring during the PVARP but outside the PVAB are sensed and counted but not tracked. A P-wave (e.g. Ps4) occurring outside PVARP is sensed and tracked, and initiates a PV delay interval.

VREF refers to a ventricular refractory period which is initiated by the onset of the ventricular stimulation pulse Vp1 (or the sensing of an R-wave). In this example, the VREF is programmable and may range between approximately 125 msec and 275 msec. All ventricular events occurring during the VREF blanking period are neither sensed nor tracked and the control system 30 issues a noise response. Usually, when the pacemaker 10 is operating in a DDD mode, PVARP is longer than VREF to prevent the sensing of an R-wave on an atrial channel by means of the electrode 18, and to prevent the corresponding initiation of a PV delay.

PVAB refers to a post ventricular atrial blanking period which is initiated by the onset of the ventricular stimulation pulse Vp1 (or the sensing of an R-wave). In this example, PVAB is programmable and may range between approximately 20 msec and 200 msec. Preferably, PVAB ranges between approximately 50 msec and 200 msec. All atrial events (e.g. Ps2) occurring during the PVAB are neither sensed nor tracked.

ABS. REF. refers to an absolute refractory period which is initiated by the onset of the ventricular stimulation pulse Vp1 (or the sensing of an R-wave). In this example, the ABS. REF. period is set to a fixed value by the pacemaker manufacturer regardless of the pacemaker mode of operation. The ABS. REF. period may be approximately 60 msec long. All atrial and ventricular events occurring during the ABS. REF. period are neither sensed nor tracked.

Returning now to FIG. 2, if at step 134 the control system 30 determines that the pacemaker 10 is currently in the primary mode of operation, the control system 30 proceeds to a decision step 136 and determines if the FAR determined using the rate smoothing filter subroutine is greater than the ATDR. If the FAR is greater than the ATDR, the control system 30 determines that a pathologic arrhythmia (e.g., atrial tachycardia, fibrillation, or flutter) is most likely occurring. The program then proceeds to step 138, at which the control system 30 acts to terminate atrial tracking ventricular pacing by switching the pacemaker 10 from the primary atrial tracking mode of operation to an alternate non-atrial tracking mode.

The present invention is mainly described herein in term of a DDD or DDDR primary mode of operation, and further in term of a DDI or DDIR alternate mode of operation. It should however be clear to a person of ordinary skill in the art that the primary mode of operation can, for example, be any suitable atrial tracking mode such as VDD, or VDDR. It should also be clear that the alternate mode of operation can, for example, be any suitable non-atrial tracking mode such as VDI or VDIR.

At step 138 the control system 30 also deactivates the primary mode program "flag", and synchronously proceeds to step 139. At step 139, the control system 30 automatically shortens a post ventricular atrial refractory period (PVARP) to a minimum, predefined (or programmable) value. The pacemaker 10 maintains this shortened refractory period (PVARP) until it switches back to its primary mode of operation or to another selected or programmed mode. Preferably, the shortened refractory period is set equal to the PVAB. However, in another embodiment, the shortened refractory period is set equal to a predefined value (e.g. 70 msec). In other embodiment, the control system 30 selects the setting of the PVARP to be either equal to PVAB or to a different fixed minimum value (e.g. 70 msec).

Figure 4:
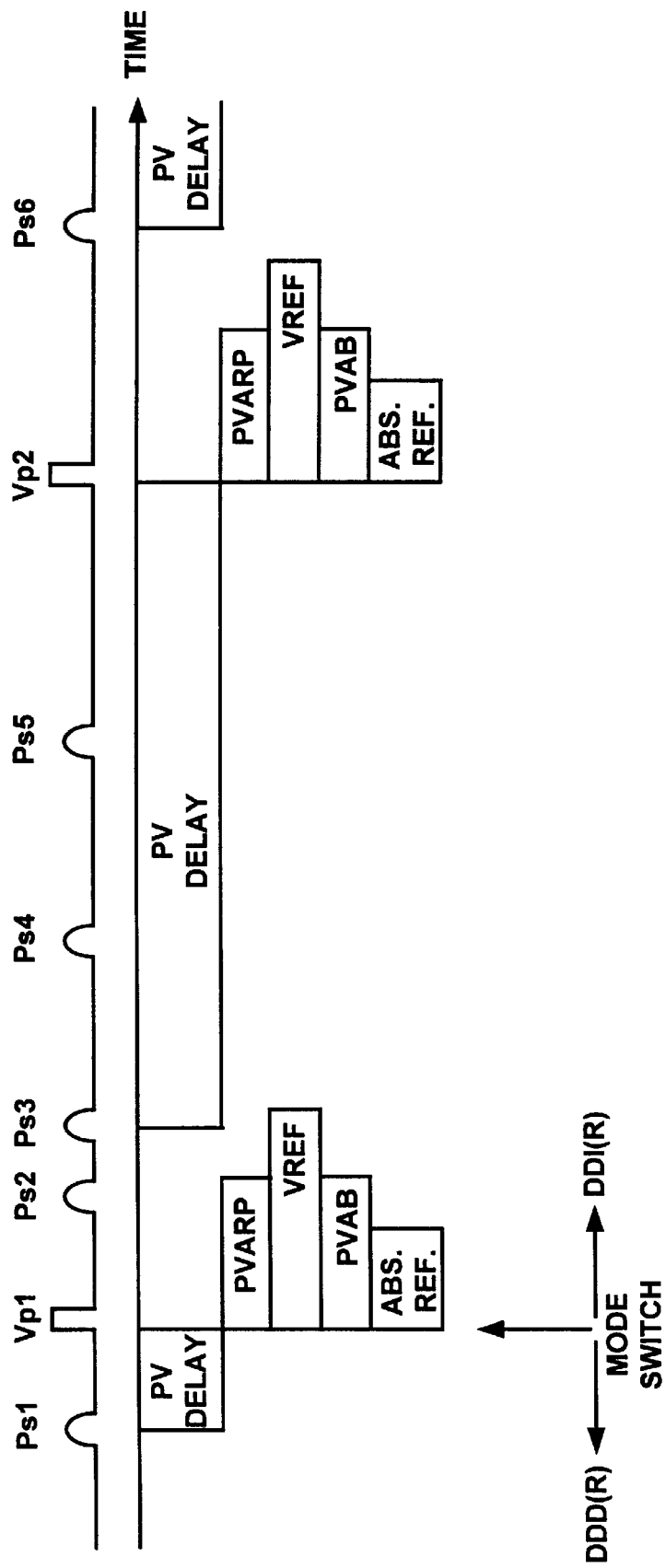
FIG. 4 is a timing diagram that illustrates the switching of the pacemaker of FIG. 1 from the primary atrial tracking DDD(R) mode of operation shown in FIG. 3, to an alternate non-atrial tracking DDI(R) mode of operation according to the present invention.

A DDI(R) alternate mode of operation is illustrated in FIG. 4. The onset of the ventricular stimulation pulse Vp1 (or the sensing of an R-wave) causes the pacemaker 10 to switch its mode of operation from the primary mode to the alternate mode as explained above in connection with step 138, and further causes the PVARP to be shortened as explained above in connection with step 139.

All atrial events (e.g. Ps2) occurring during the PVARP, which, in this illustration is set equal to the PVAB, are neither tracked nor sensed. Since the pacemaker 10 is operating in a non-atrial tracking mode (e.g. DDI), all P-waves occurring outside the PVARP are sensed but are not tracked. The first P-wave (e.g. Ps3) occurring outside the PVARP atrial stimulation, inhibits atrial pacing and minimizes the likelihood of atrial pacing competition.

The control system 30 (FIG. 1) counts the P-waves (e.g. Ps4, Ps5) occurring outside the PVARP, within the PV delay interval, to determine the end of the pathologic arrhythmia. Thus, the pacemaker 10 can now obtain an accurate measurement of the atrial rate during pathological arrhythmia, respond promptly to the termination of the pathologic arrhythmia, and resume the normal pacing operation.

At step 140 the control system 30 can, synchronously with the execution of step 138, automatically change one or more selected primary operational parameters to corresponding alternate operational parameters from settings appropriate to the primary mode to settings appropriate to the alternate mode. For example, the control system 30 can automatically modify a primary (or base) pacing rate to a higher alternate pacing rate setting. In a preferred embodiment, the alternate pacing rate, that is the interval between two consecutive ventricular stimulation pulses (e.g. Vp1 and Vp2) is approximately 5 to 35 pulses per minute (ppm) higher than the primary pacing rate. This feature will help suppress atrial pacing competition and minimize mode switch lockup.

Since the primary operational parameters are usually optimized for performance in the primary mode, it would be desirable to switch these parameters to alternate operational parameters when the mode is switched from the primary mode to the alternate mode at step 138, and the PVARP is automatically set equal to the PVAB at step 139. It should be clear that the alternate operational parameters are not limited to the base rate, and may additionally include alternate ventricular pulse width, atrial and ventricular refractory periods, and atrial and ventricular sense configurations. These alternate operational parameters can be programmed by the external programming system 52 at the time of implantation or during the patient's follow-up visits.

Figure 5:
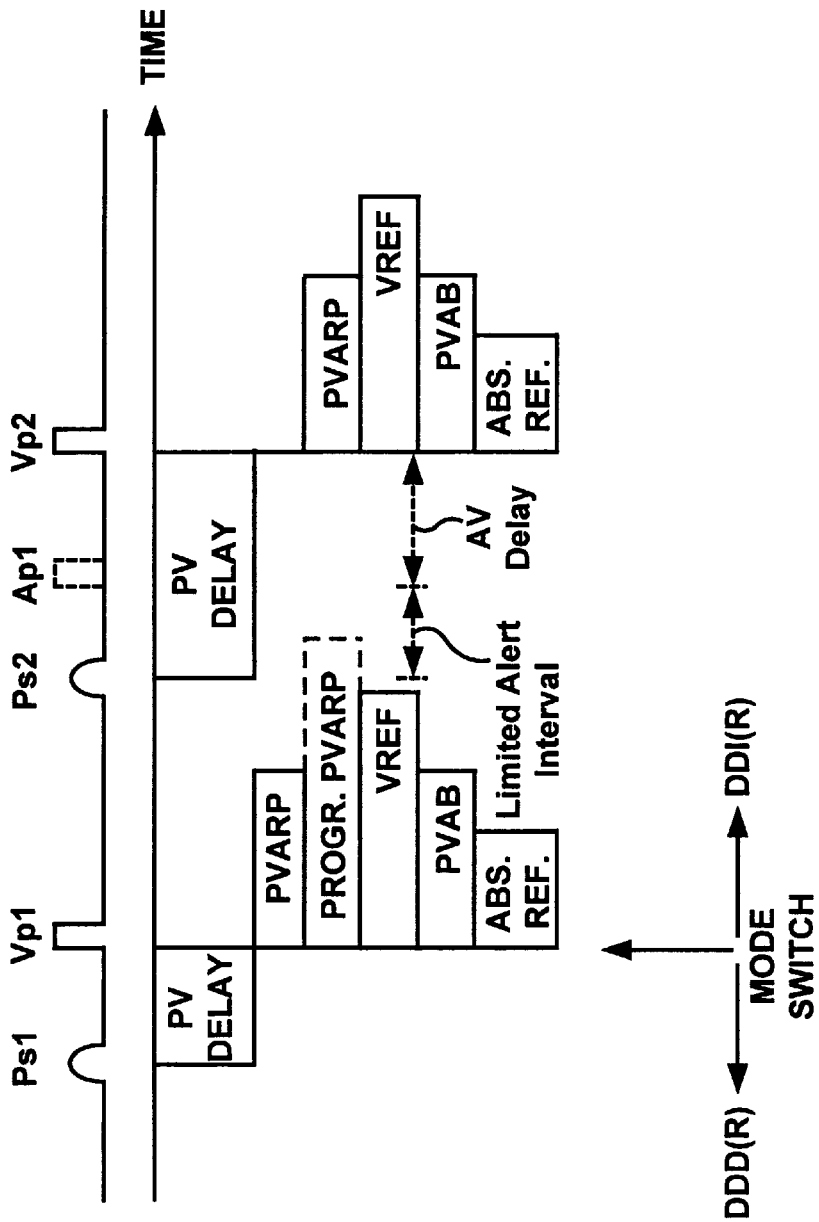
FIG. 5 is a timing diagram that illustrates the switching of the pacemaker of FIG. 1 from the primary atrial tracking DDD(R) mode of operation shown in FIG. 3, to an alternate non-atrial tracking DDI(R) mode of operation and to an alternate pacing rate according to the present invention.

FIG. 5 illustrates the suppression of atrial pacing competition with automatic PVARP and pacing rate adjustment accompanying the mode switch operation, as explained herein in connection with steps 138, 139, 140 (FIG. 2). When mode switching is accompanied by a modification of the pacing rate without the shortening of the PVARP, as illustrated by the block labeled "PROGR. PVARP", which is an abbreviation for "PPROGRAMMED PVARP", a P-wave Ps2 occurring within the "PROGR. PVARP" block does not inhibit atrial pacing, and an atrial stimulation pulse (e.g. Ap1) is initiated at the end of a limited alert interval, increasing the chance of atrial competition. In turn, the atrial stimulation pulse Ap1 sets an AV delay interval. A ventricular stimulation pulse Vp2 is triggered at the end of the AV delay interval.

However, the shortened PVARP (shown in solid line) according to the present invention allows the P-wave Ps2 to inhibit atrial pacing, effectively extending the atrial alert interval.

The control system 30 records, at step 142, the automatic mode switch event at step 138, the automatic shortening of the PVARP at step 139, and the modification to alternate operational parameters at step 140, along with associated data, into the memory 44. The recorded associated data may include, but are not limited to, the maximum FAR achieved during the mode switch, the duration of the mode switch, and the time and date of the execution of steps 138, 139 and 140.

The control system 30 completes the loop by returning to step 100 for processing the next cardiac cycle. If, at the decision step 134 the control system 30 determines that the pacemaker 10 is not currently in the primary mode of operation, the control system 30 proceeds to a decision step 144. At the decision step 144 the control system 30 determines if the FAR obtained from the rate smoothing filter subroutine is less than or equal to the MTR. If the FAR is not less than or equal to the MTR, the control system 30 returns to step 100 for processing the next cardiac cycle.

If at decision step 144 the control system 30 determines that the FAR is less than or equal to the MTR, it proceeds to step 146 and switches the mode of operation of the pacemaker 10 from the alternate mode to the primary mode of operation (or to another appropriate mode). The MTR is set as the criterion for switching back to the primary mode in order to enable the primary mode to be dominant and thus maintain A-V synchrony even at a high pacing rate. This criterion is particularly beneficial to patients with normally high atrial rates. Switching to the primary mode when the FAR falls below the MTR advantageously avoids frequent mode switching, which may occur when identical thresholds for switching to and from the primary mode are used. At step 146 the control system 30 also activates the primary mode program "flag."

Synchronously with the execution of step 146, the control system 30 changes the operational parameters from the alternate mode settings to the primary mode settings at step 148. For example, the PVARP is extended to its primary mode value. Since the primary operational parameter settings are usually optimized for performance in the primary mode, it would be desirable to switch the settings to the primary operational parameter settings when the mode is switched from alternate mode to the primary mode at step 146.

Figure 6:
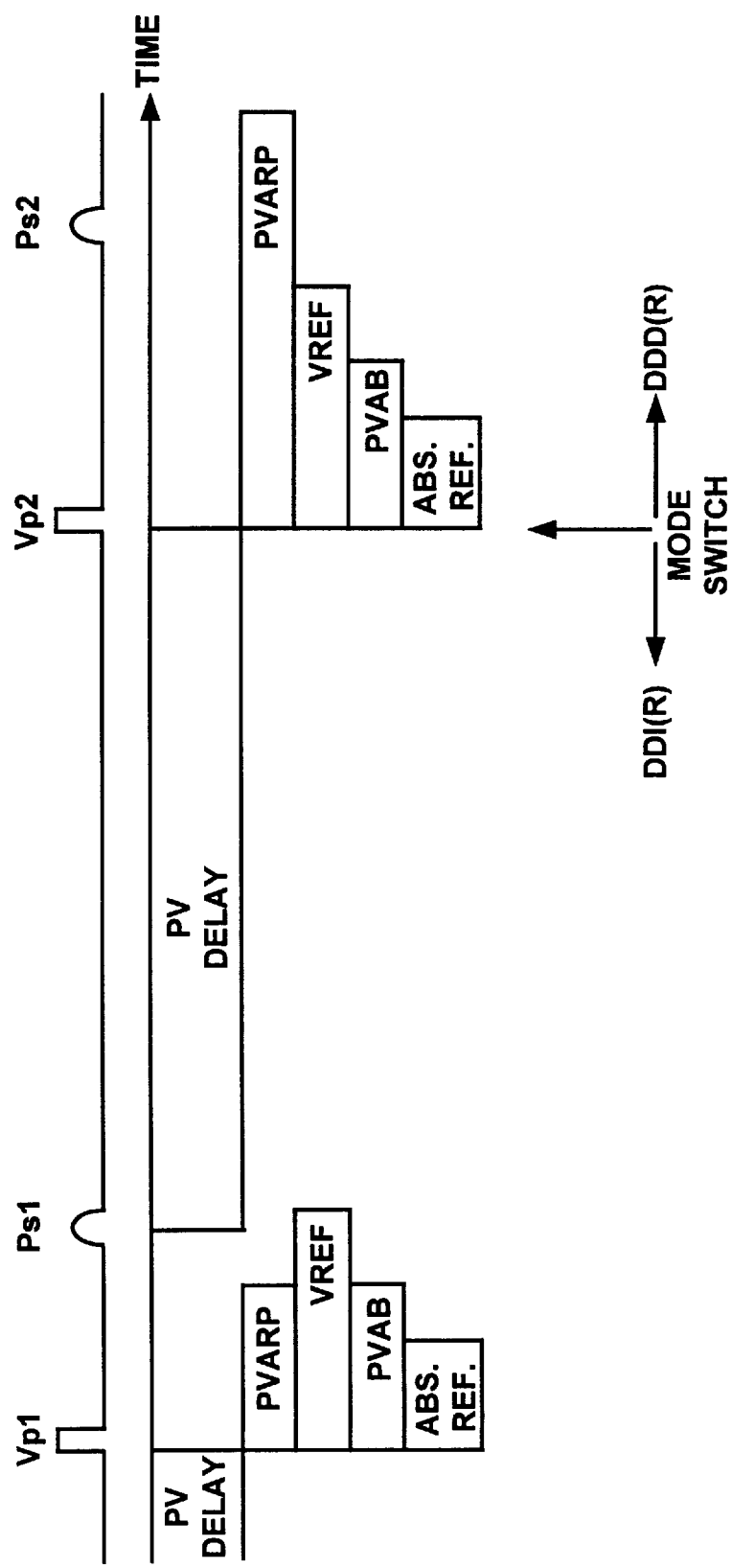
FIG. 6 is a timing diagram that illustrates the switching of the pacemaker of FIG. 1 from the alternate non-atrial tracking DDI(R) mode of operation shown in FIG. 4, to the primary atrial tracking DDD(R) mode of operation shown according to the present invention.

FIG. 6 is a timing diagram that illustrates the switch from the alternate mode to the primary mode of operation (step 146), and the modification to primary operational parameters (step 148), at the onset of the ventricular stimulation pulse Vp2, or alternatively upon sensing an R-wave, The program then proceeds to step 142 where the control system 30 records the mode switch event of step 146, along with associated data, into the memory 44. The recorded data may include, but are not limited to, the maximum FAR achieved during the mode switch, the duration of the mode switch, the variance of individual atrial and ventricular events during the mode switch (to indicate the type of pathologic arrhythmia triggering the mode switch), and the time and date of the switch. The control system 30 then returns to step 100 for processing the next cardiac cycle.

One skilled in the art will appreciate that the present invention can be practiced by other than the described embodiments or values, which are presented for purposes of illustration and not of limitation.

What is claimed is:

1. A pacemaker having a plurality of selectable modes of operation including a primary mode and an alternate mode, the pacemaker comprising:

a pulse generator for generating stimulation pulses;

a control system connected to the pulse generator;

the control system automatically switching the mode of operation from the primary mode to the alternate mode upon detection of a predetermined condition;

the control system further automatically shortening a post ventricular atrial refractory period (PVARP) to a minimum value, synchronously with the automatic switching to the alternate mode of operation;

the control system maintaining the shortened PVARP until the termination of the predetermined condition; and the control system automatically switching to the primary mode of operation, synchronously with the termination of the predetermined condition.

2. The pacemaker, according to claim 1, wherein the primary mode comprises an atrial tracking mode and the alternate mode comprises a non-atrial tracking mode.

3. The pacemaker, according to claim 2, wherein the shortened PVARP is set equal to a post ventricular atrial blanking period (PVAB).

4. The pacemaker, according to claim 3, wherein the PVAB ranges between approximately 20 msec and 200 msec.

5. The pacemaker, according to claim 4, wherein the PVAB ranges between approximately 50 msec and 200 msec.

6. The pacemaker, according to claim 3, wherein the primary mode is selected from the group of: DDD, DDDR, VDD, VDDR, DDT or DDTR mode.

7. The pacemaker, according to claim 3, wherein the alternate mode selected from the group of: DDI, DDIR, VDI, VDIR, DDT or DDTR mode.

8. The pacemaker, according to claim 3, wherein the predetermined condition includes an atrial tachycardia.

9. The pacemaker, according to claim 3, further comprising a memory in which the control system stores data pertaining to changes in the mode of operation of the pacemaker.

10. The pacemaker, according to claim 3, further comprising a telemetry circuit connected to the control system; and wherein the telemetry circuit is selectively coupled to a programming device by way of a communication link.

11. The pacemaker, according to claim 3, further comprising a filter for filtering an intrinsic atrial rate; and wherein the control system includes a rate smoothing filter subroutine for smoothing the filtered atrial rate to minimize the effect of electrical noise.

12. The pacemaker, according to claim 3, wherein the primary mode is associated with a primary set of operational parameters including a primary pacing rate.

13. The pacemaker, according to claim 3, wherein the alternate mode is associated with an alternate set of operational parameters including an alternate pacing rate.

14. The pacemaker, according to claim 13, wherein the alternate pacing rate is approximately between 5 to 35 pulses per minute higher than the primary pacing rate.

15. The pacemaker, according to claim 3, wherein the primary mode includes a dual chamber mode.

16. The pacemaker, according to claim 3, wherein the alternate mode includes a dual chamber mode.

17. The pacemaker, according to claim 2, wherein the shortened PVARP is selectively set equal to either a post ventricular atrial blanking period (PVAB) or to a predetermined value.

18. The pacemaker, according to claim 17, wherein the predetermined value is approximately 70 msec.

19. The stimulation device, according to claim 1, wherein the predetermined value is approximately 70 msec.

20. A method of operating a pacemaker having a plurality of selectable modes of operation comprising a primary mode and an alternate mode, a pulse generator for generating stimulation pulses, and a control system for controlling the operation of the pacemaker, the method comprising:

automatically switching the mode of operation from the primary mode to the alternate mode upon detection of a predetermined condition;

automatically shortening a post ventricular atrial refractory period (PVARP) to a minimum value, synchronously with the automatic switching to the alternate mode of operation;

maintaining the shortened PVARP until the termination of the predetermined condition; and automatically switching to the primary mode of operation, synchronously with the termination of the predetermined condition.

21. The method, according to claim 20, wherein automatically switching the mode of operation from the primary mode to the alternate mode includes switching from a primary, atrial tracking mode to an alternate non-atrial tracking mode.

22. The method, according to claim 21, wherein automatically switching to the primary mode includes switching from an alternate non-atrial tracking mode to a primary, atrial tracking mode.

23. The method, according to claim 22, wherein shortening the PVARP includes setting the PVARP equal to a post ventricular atrial blanking period (PVAB).

24. The method, according to claim 23, wherein setting the PVARP equal to the PVAB includes setting the PVARP to a value ranging between approximately 20 msec and 200 msec.

25. The method, according to claim 24, wherein setting the PVARP equal to the PVAB includes setting the PVARP to a value ranging between approximately 50 msec and 200 msec.

26. The method, according to claim 25, wherein switching from the primary mode includes switching from any one of: DDD, DDDR, VDD, VDDR, DDT or DDTR mode.

27. The method, according to claim 26, wherein switching from the alternate mode includes switching from any one of: DDI, DDIR, VDI, VDIR, DDT or DDTR mode.

28. The method, according to claim 23, further including storing data pertaining to changes in the mode of operation of the pacemaker in a memory.

29. The method, according to claim 23, further including filtering an intrinsic atrial rate; and calling a rate smoothing filter subroutine for smoothing the filtered atrial rate to minimize the effect of electrical noise.

30. The method, according to claim 23, wherein the primary mode is associated with a primary set of operational parameters including a primary pacing rate;

wherein the alternate mode is associated with an alternate set of operational parameters including an alternate pacing rate; and further including setting the alternate pacing rate to a value that ranges between approximately between 5 to 35 pulses per minute higher than the primary pacing rate.

31. The method, according to claim 22, wherein shortening the PVARP includes selectively setting the PVARP equal to either a post ventricular atrial blanking period (PVAB) or to a predetermined value.

32. The method, according to claim 31, wherein shortening the PVARP includes selectively setting the PVARP equal to either a post ventricular atrial blanking period (PVAB) or to approximately 70 msec.

33. A stimulation device having a plurality of selectable modes of operation including a primary mode and an alternate mode, the stimulation device comprising:

a pulse generator for generating stimulation pulses;

control means connected to the pulse generator;

the control means automatically switching the mode of operation from the primary mode to the alternate mode upon detection of a predetermined condition;

the control means further automatically shortening a post ventricular atrial refractory period (PVARP) to a minimum value, synchronously with the automatic switching to the alternate mode of operation;

the control means maintaining the shortened PVARP until the termination of the predetermined condition; and the control means automatically switching to the primary mode of operation, synchronously with the termination of the predetermined condition.

34. The stimulation device, according to claim 33, wherein the primary mode includes an atrial tracking mode and the alternate mode comprises a non-atrial tracking mode.

35. The stimulation device, according to claim 33, wherein the shortened PVARP is set equal to a post ventricular atrial blanking period (PVAB).

36. The stimulation device, according to claim 35, wherein the PVAB ranges between approximately 20 msec and 200 msec.

37. The stimulation device, according to claim 36, wherein the PVAB ranges between approximately 50 msec and 200 msec.

38. The stimulation device, according to claim 35, wherein the primary mode is selected from the group of: DDD, DDDR, VDD, VDDR, DDT or DDTR mode.

39. The stimulation device, according to claim 35, wherein the alternate mode selected from the group of: DDI, DDIR, VDI, VDIR, DDT or DDTR mode.

40. The stimulation device, according to claim 35, wherein the predetermined condition includes an atrial tachycardia.

41. The stimulation device, according to claim 35, further comprising a memory in which the control means stores data pertaining to changes in the mode of operation of the stimulation device.

42. The stimulation device, according to claim 35, further comprising a telemetry circuit connected to the control means; and wherein the telemetry circuit is selectively coupled to a programming device by way of a communication link.

43. The stimulation device, according to claim 35, further comprising a filter for filtering an intrinsic atrial rate; and wherein the control means includes a rate smoothing filter subroutine for smoothing the filtered atrial rate to minimize the effect of electrical noise.

44. The stimulation device, according to claim 35, wherein the primary mode is associated with a primary set of operational parameters including a primary pacing rate.

45. The stimulation device, according to claim 35, wherein the alternate mode is associated with an alternate set of operational parameters including an alternate pacing rate.

46. The stimulation device, according to claim 45, wherein the alternate pacing rate is approximately between 5 to 35 pulses per minute higher than the primary pacing rate.

47. The stimulation device, according to claim 35, wherein the primary mode includes a dual chamber mode.

48. The stimulation device, according to claim 35, wherein the alternate mode includes a dual chamber mode.

49. The stimulation device, according to claim 34, wherein the shortened PVARP is selectively set equal to either a post ventricular atrial blanking period (PVAB) or to a predetermined value.

* * * * *